United States Patent
Zhang et al.

(10) Patent No.: US 11,628,199 B2
(45) Date of Patent: Apr. 18, 2023

(54) MEDICINE FOR COMBINED USE IN CANCER TREATMENT

(71) Applicant: SICHUAN JIUZHANG BIOLOGICAL SCIENCE AND TECHNOLOGY CO., LTD, Sichuan (CN)

(72) Inventors: Jie Zhang, Sichuan (CN); Wang Huang, Sichuan (CN); Huarong Yang, Sichuan (CN)

(73) Assignee: SICHUAN JIUZHANG BIOLOGICAL SCIENCE AND TECHNOLOGY CO., LTD, Sichuan (CN)

( * ) Notice: Subject to any disclaimer, the term of this patent is extended or adjusted under 35 U.S.C. 154(b) by 100 days.

(21) Appl. No.: 16/641,197

(22) PCT Filed: Aug. 17, 2018

(86) PCT No.: PCT/CN2018/101172
§ 371 (c)(1),
(2) Date: Feb. 21, 2020

(87) PCT Pub. No.: WO2019/037671
PCT Pub. Date: Feb. 28, 2019

(65) Prior Publication Data
US 2020/0215150 A1    Jul. 9, 2020

(30) Foreign Application Priority Data
Aug. 21, 2017 (CN) .......................... 201710719622.3

(51) Int. Cl.
*A61K 31/216* (2006.01)
*A61K 31/565* (2006.01)
*A61K 38/09* (2006.01)
*A61P 35/00* (2006.01)

(52) U.S. Cl.
CPC .......... *A61K 38/09* (2013.01); *A61K 31/216* (2013.01); *A61K 31/565* (2013.01); *A61P 35/00* (2018.01)

(58) Field of Classification Search
CPC ...... A61P 35/00; A61K 31/216; A61K 31/565
See application file for complete search history.

(56) References Cited

FOREIGN PATENT DOCUMENTS

| CN | 101120936 A | * | 2/2008 |
|---|---|---|---|
| CN | 101120936 A | | 2/2008 |
| CN | 103690935 A | | 4/2014 |
| CN | 104758277 A | | 7/2015 |
| CN | 105310988 A | | 2/2016 |
| CN | 106890169 A | | 6/2017 |
| CN | 107441076 A | | 12/2017 |
| WO | 2008153318 A2 | | 12/2008 |

OTHER PUBLICATIONS

Duffy, Michael. Clinical Chemistry 2005, 51:3, 494-503. (Year: 2005).*
Internet webpage printout of WayBack Machine search for "MCF7.com", downloaded and printed Feb. 10, 2021. (Year: 2021).*
Internet webpage printout of MCF7.com, downloaded and printed Feb. 10, 2021. (Year: 2010).*
Lee and Zhu, Carcinogenesis vol. 27 No. 2 pp. 269-277, 2006 (Year: 2006).*
Internet webpage printout of MCF7.com, capture from May 16, 2010 on the Internet Archive Wayback Machine. (Year: 2010).*
Deka et al, Current Molecular Medicine, vol. 17 (1), Jan. 1, 2017, pp. 79-89(11). (Year: 2017).*
Belagali et al, European Oncology & Haematology, 2016;12(1):44-50 (Year: 2016).*

* cited by examiner

*Primary Examiner* — Jared Barsky
*Assistant Examiner* — Janet L Coppins
(74) *Attorney, Agent, or Firm* — Novick, Kim & Lee, PLLC; Allen Xue

(57) ABSTRACT

A medicine for combined use in cancer treatment, comprising chlorogenic acid and a hormone drug which have unit preparations of the same or different specifications and which are administered either together or separately, as well as comprising a pharmaceutically acceptable carrier. The combined use of the chlorogenic acid and hormone drug achieves the effects of synergistic interaction, which thus overcome the defects of single drug treatment, such as a major toxic side effect and a poor treatment outcome and may reverse the drug resistance to hormone drugs and has good prospects for clinical application.

3 Claims, No Drawings

MEDICINE FOR COMBINED USE IN CANCER TREATMENT

TECHNICAL FIELD

The present invention relates to a combined medicine for treatment of cancer, and belongs to the biotherapeutic medicinal field.

BACKGROUND ART

Cancer is a major public health problem that is necessarily solved in China and even all regions of the world. The average number of people diagnosed with cancer per year is millions, and the cancers include more than 200 types. At present, cancer has become one of the main diseases causing death of people. But, due to the poor selectivity of anti-malignant tumor drugs, the single drug treatment has the disadvantages of great toxic side actions or poor treatment effects. Therefore, the research on a new generation of low-toxic and high-effective drugs has become an urgent need for malignant tumor treatment.

Chlorogenic acid is a condensed phenolic acid formed by condensation of caffeic acid and quinic acid, and also called caffeotannic acid, with a chemical name of 3-o-caffeoylquinic acid and a molecular formula of $C_{16}H_{18}O_9$. Chlorogenic acid is a natural substance with strong biological activity, and current clinical trials have confirmed that chlorogenic acid is safe and non-toxic, as well as has anti-cancer and cancer-suppressor effects.

Hormone drugs denote those that have the ability of binding to cytosolic protein and nucleoprotein hormone receptors, forming a hormone-receptor complex with high affinity and specificity, being activated and entering the nucleus to interact with various components, causing DNA replication and cell division by a series of enzyme reactions, thereby affecting the physiological functions of cells.

In the present invention, anti-tumor medicines are prepared by combination of chlorogenic acid and hormone drugs, and said medicines have significant therapeutic effect on breast, prostate, ovarian or cervical cancers, and solve the problems that the single drug has poor treatment effects and great toxic side actions.

CONTENT OF THE INVENTION

In order to solve above problems, the present invention provides a drug combination of chlorogenic acid and hormone drugs, as well as the use of chlorogenic acid and hormone drugs in the preparation of drug combinations for treatment of cancers.

The present invention provides a drug combination for treatment of cancers, and it contains chlorogenic acid and hormone drugs in unit preparations of the same or different specifications that are simultaneously or separately administrated, as well as pharmaceutically acceptable carriers.

Wherein, said hormone drugs include but not limited to fulvestrant, abarelix, and degarelix.

Preferably, the weight ratio of said chlorogenic acid and hormone drugs is 10:1-1:10; more preferably, the weight ratio is 8:3-1:4; further preferably, the weight ratio is 2:3-1:3.

Wherein, said preparation of drug combination is an injectable or oral formulation of drugs containing 10 mg-240 mg chlorogenic acid.

The present invention also provides the use of chlorogenic acid and hormone drugs in the preparation of combined medicines for treatment of cancers.

Wherein, said hormone drugs include but not limited to fulvestrant, abarelix, and degarelix.

Preferably, the weight ratio of said chlorogenic acid and hormone drugs is 10:1-1:10; more preferably, the weight ratio is 8:3-1:4; further preferably, the weight ratio is 2:3-1:3.

Wherein, said drugs for treatment of cancers are those used for treating breast, prostate, ovarian or cervical cancers Wherein, said cancer is that having developed resistance; preferably, said cancer is prostate cancer.

The present invention also provides a method for treatment of cancer, characterized in that it includes simultaneously or respectively administrating chlorogenic acid and hormone drugs in unit preparations of same or different specifications.

Wherein, said hormone drugs include but not limited to fulvestrant, abarelix, and degarelix.

Preferably, the weight ratio of said chlorogenic acid and hormone drugs is 10:1-1:10; more preferably, the weight ratio is 8:3-1:4; further preferably, the weight ratio is 2:3-1:3.

Wherein, said preparation of drug combination is an injectable or oral formulation of drugs containing 10 mg-240 mg chlorogenic acid.

Beneficial effects achieved by the present invention: the present invention provides the combined use of chlorogenic acid and hormone drugs for treating cancers, and the combined use achieves the effects of synergistic interaction, overcomes the defects that the single drug has great toxic side actions and poor treatment effects. The combination of chlorogenic acid and hormone drugs has excellent therapeutic effect and low toxicity, can reverse the resistance of hormone drugs, and has good clinical application prospects.

In the following, the present invention is further illustrated by referring to the specific examples, but the present invention is not limited. Based on above contents of the present invention, without departing from above basic technical spirit of the present invention, various modifications, alternations or changes, made according to the common technical knowledge and conventional means in the art, can also be realized.

EXAMPLES

Example 1 In Vivo Animal Experiments on the Combination of Chlorogenic Acid and Fulvestrant for Treating Breast Cancer in Mice 1. Material Test drug: chlorogenic acid, fulvestrant.
Test cell lines: EMT-6 mouse breast cancer cell lines.
Test animals: BALB/C-nu mice, ♀, weight 16-21 g.

2. Experimental Method.

Cells in exponential phase of growth were taken out, digested with trypsin to remove the cell wall, and then cell suspension was prepared by addition of saline. The prepared cell suspension was inoculated under the left anterior armpit of mice at 0.2 ml/mouse (about $1 \times 10^6$ cells), and the mice were randomly divided into four groups as weight, i.e. fulvestrant group, chlorogenic acid group, fulvestrant+chlorogenic acid group, and the negative control group, respectively, each group having 6 mice.

Fulvestrant group received drug once by intraperitoneal injection on the next day after inoculation; chlorogenic acid group received drug once every day by intraperitoneal injection from the next day after inoculation, and the drug was successively administrated 15 times; combined medicine group received intraperitoneal injection of fulvestrant once on the next day after inoculation, and intraperitoneal injection of chlorogenic acid once every day from the next day after inoculation; the negative control group received saline by intraperitoneal injection once every day from the next day after inoculation, and saline was continuously given 15 times. When the tumor volume in the negative group was about 0.5 cm$^3$, the experiment was stopped. The mice were sacrificed by cervical dislocation and weighed. The tumors were removed and weighed to calculate the tumor suppression rate.

3. Data Processing (1) tumor inhibition rate %=[1−(the average tumor weight in the test group/the average tumor weight in the negative group)]×100%

(2) If both drugs are combined, Q=E(a+b)/(Ea+Eb−Ea×Eb), in which E(a+b) is the inhibition rate for the combination of two drugs, i.e. the tested combined effect; Ea and Eb is respectively the inhibition rates of two drugs when they are separately used; the denominator (Ea+Eb−Ea×Eb) is the expected combined effect. When Q value is 0.85-1.15, the combined effect of both drugs is added up (+); When Q value is 1.15-20, the combined effect of both drugs is synergistic (++); When Q value is >20, the synergistic effect is obvious (+++); When Q value is 0.05-0.85, the combined effect of both drugs is antagonistic; when Q value is <0.05, the antagonistic effect is obvious.

4. Experimental Results

For the effect of the combination of chlorogenic acid and fulvestrant on mouse xenograft tumor inhibition, the results are shown in Table 1.

TABLE 1

Effect of the combined drug on inhibition of mouse xenograft tumor of EMT-6 breast cancer.

| Groups | Dosage (mg · kg$^{-1}$) | Tumor weight (g) | Tumor inhibitory rate (%) | Q value |
|---|---|---|---|---|
| chlorogenic acid group | 10 | 0.897 ± 0.346* | 31.94 | — |
| | 20 | 0.831 ± 0.221* | 36.95 | — |
| | 40 | 0.764 ± 0.539* | 42.03 | — |
| The combined drug group | Fulvestrant 40 + chlorogenic acid 10 | 0.267 ± 0.174** | 79.74 | 1.297 |
| | Fulvestrant 40 + chlorogenic acid 20 | 0.209 ± 0.352** | 84.14 | 1.308 |
| | Fulvestrant 40 + chlorogenic acid 40 | 0.228 ± 0.209** | 82.70 | 1.231 |
| Fulvestrant group | 40 | 0.746 ± 0.311* | 43.40 | — |
| Negative control group | N.S | 1.318 ± 0.731 | — | — |

Compared with the negative control group,
*p < 0.05,
**p < 0.01.

For the combined use of 40 mg/kg fulvestrant with 10 mg/kg, 20 mg/kg, 40 mg/kg chlorogenic acid, Q values for inhibition of mouse tumor of EMT-6 breast cancer are 1.231-1.308 and locate in the range of 1.15-20, and thus both drugs have synergistic effect.

Example 2 In Vivo Animal Experiments on the Combination of Chlorogenic Acid and Barelix or Degarelix for Treating Prostate Cancer in Mice 1. Material Test drug: chlorogenic acid, abarelix, degarelix.

Test cell lines: RM-1 mouse prostate cancer cell lines.

Test animals: Kunming mice, ♂, weight 17-24 g.

2. Experimental Method

Cells in exponential phase of growth were taken out, digested with trypsin to remove the cell wall, and then cell suspension was prepared by addition of saline. The prepared cell suspension was inoculated under the left anterior armpit of mice at 0.2 ml/mouse (about 1×10$^6$ cells), and the mice were randomly divided into six groups as weight, i.e. abarelix group, degarelix group, chlorogenic acid group, abarelix+chlorogenic acid group, degarelix+chlorogenic acid group, and the negative control group, respectively, each group having 6 mice.

Abarelix group received drug once by intraperitoneal injection on the next day after inoculation; degarelix group received drug once by subcutaneous injection on the next day after inoculation; chlorogenic acid group received drug once every day by intraperitoneal injection from the next day after inoculation, and the drug was successively administrated 15 times; abarelix+chlorogenic acid group received abarelix once by intraperitoneal injection on the next day after inoculation, and received chlorogenic acid once every day by intraperitoneal injection from the next day after inoculation, and chlorogenic acid was administrated 15 times; degarelix+chlorogenic acid group received degarelix once by subcutaneous injection on the next day after inoculation, and received chlorogenic acid once every day by intraperitoneal injection from the next day after inoculation, and chlorogenic acid was administrated 15 times; the negative control group received saline by intraperitoneal injection once every day from the next day after inoculation, and saline was continuously given 15 times. When the tumor volume in the negative group was about 0.5 cm$^3$, the experiment was stopped. The mice were sacrificed by cervical dislocation and weighed. The tumors were removed and weighed to calculate the tumor inhibitory rate.

3. Data Processing

The data processing is same to that in example 1.

4. Experimental Results

For the effect of the combination of chlorogenic acid and abarelix or degarelix on mouse xenograft tumor inhibition, the results are shown in Table 2.

TABLE 2

Effect of the combined drug on inhibition of mouse xenograft tumor of prostate cancer.

| Groups | Dosage (mg · kg$^{-1}$) | Tumor weight (g) | Tumor inhibitory rate (%) | Q value |
|---|---|---|---|---|
| chlorogenic acid group | 10 | 1.175 ± 0.117 | 24.05 | — |
| | 20 | 1.116 ± 0.358 | 27.86 | — |
| | 40 | 1.105 ± 0.641 | 28.57 | — |
| abarelix + chlorogenic acid group | abarelix15 + chlorogenic acid10 | 0.275 ± 0.419** | 82.22 | 1.455 |
| | abarelix15 + chlorogenic acid20 | 0.241 ± 0.303** | 84.42 | 1.439 |
| | abarelix15 + chlorogenic acid40 | 0.264 ± 0.16**1 | 82.93 | 1.404 |

TABLE 2-continued

Effect of the combined drug on inhibition of
mouse xenograft tumor of prostate cancer.

| Groups | Dosage (mg · kg⁻¹) | Tumor weight (g) | Tumor inhibitory rate (%) | Q value |
|---|---|---|---|---|
| degarelix + chlorogenic acid group | degarelix30 + chlorogenic acid10 | 0.238 ± 0.224** | 84.62 | 1.354 |
| | degarelix30 + chlorogenic acid20 | 0.204 ± 0.193** | 86.81 | 1.349 |
| | degarelix30 + chlorogenic acid20 | 0.211 ± 0.462** | 86.36 | 1.334 |
| Abarelix group | 15 | 0.886 ± 0.521* | 42.73 | — |
| Degarelix group | 30 | 0.764 ± 0.218* | 50.61 | — |
| Negative control group | N.S | 1.547 ± 0.258 | — | — |

Compared with the negative control,
*p < 0.05,
**p < 0.01.

For the combined use of 15 mg/kg abarelix with 10 mg/kg, 20 mg/kg, 40 mg/kg chlorogenic acid, Q values for inhibition of mouse xenograft tumor of RM-1 prostate cancer are 1.334-1.354 and locate in the range of 1.15-20, indicating both drugs have synergistic effect.

For the combined use of 30 mg/kg degarelix with 10 mg/kg, 20 mg/kg, 40 mg/kg chlorogenic acid, Q values for inhibition of mouse xenograft tumor of RM-1 prostate cancer are 1.334-1.354 and locate in the range of 1.15-20, indicating both drugs have synergistic effect.

Example 3 Animal Experiments on the Combination of Chlorogenic Acid and Abarelix Against Multi-Drug Resistant Cancers 1. Material Test drug: chlorogenic acid, abarelix.

Test cell lines: RM-1 mouse prostate cancer cell lines. RM-1 cell lines were induced by increasing concentration gradient of aberlix and established by clone and screen. Prior to experiment, cell lines were cultured without drug.

Test animals: Kunming mice, ♂, weight 17-24 g.

2. Experimental Method 2.1 Establishment of Experimental Animal Tumor Model

Drug-resistant cell lines after removal of drug were adjusted to the concentration of $1 \times 10^7$/mL with culture medium, and inoculated under the right anterior armpit of mice at 0.1 ml/mouse.

2.2 Method of Administration

After the mean diameter of tumor reached 100 mm³, mice were divided into 4 groups, i.e. abarelix group, chlorogenic acid+abarelix group, chlorogenic acid group, and the negative control group, respectively.

Abarelix group: intraperitoneal injection, once every seven days, 15 mg/kg, two doses in total.

chlorogenic acid+abarelix group: chlorogenic acid was intraperitoneally injected, once every day, 10 mg/kg, continuous administration for 5 days; After withdrawal of chlorogenic acid, abarelix was intraperitoneally injected on the next day, once every 7 days, 15 mg/kg, two doses in total.

Chlorogenic acid group: intraperitoneal injection, once every day, 10 mg/kg, continuous administration for 5 days; after that, saline was intraperitoneally injected, once every day, continuing 10 days.

Negative control group: intraperitoneal injection of saline, once every day, continuing 15 days.

2.3 Evaluation of Anti-Tumor Effect

After completion of administration, the experiment was stopped, and mice were sacrificed by cervical dislocation and weighed. The tumors were removed and weighed to calculate the tumor inhibitory rate.

3. Data Processing tumor inhibition rate %=[1−(the average tumor weight in the test group/the average tumor weight in the negative group)]×100%

4. Experimental Results

For the effect on tumor inhibition rate against drug-resistant xenograft tumors in each test group, the results are shown in Table 3.

TABLE 3

Effect on the tumor weight and the tumor inhibitory
rate of mouse xenograft tumor of drug-resistant
RM-1 prostate cancer ($\bar{x} \pm s$)

| Groups | Dosage (mg · kg⁻¹) | Animal number (n) | Tumor weight (g) | Tumor inhibitory rate (%) |
|---|---|---|---|---|
| chlorogenic acid | 10 | 8 | 2.251 ± 0.581 | 8.41 |
| abarelix | 15 | 8 | 2.339 ± 0.614 | 4.84 |
| chlorogenic acid + abarelix | chlorogenic acid10 + abarelix15 | 8 | 0.624 ± 0.632**ΔΔ | 74.54 |
| Negative control group | N.S | 8 | 2.458 ± 0.874 | — |

Compared with the negative control,
*p < 0.05,
**p < 0.01; compared with nilotinib,
Δp < 0.05,
ΔΔp < 0.01

Results indicated that in chlorogenic acid group and in abarelix group, the inhibitory rate of mouse xenograft tumor of drug-resistant RM-1 prostate cancer was weaker, without obvious suppression effect. While in chlorogenic acid+abarelix group, the inhibitory rate of mouse xenograft tumor of drug-resistant RM-1 prostate cancer was significant, indicating that chlorogenic acid can effectively solve the drug-resistance of resistant RM-1 prostate cancer.

In summary, the combination of chlorogenic acid and hormone drugs can be used for treatment of breast, prostate, ovarian or cervical cancers, and in the combination, the ratio of chlorogenic acid and hormone drugs is 8:3-1:4, preferably 2:3-1:3. Compared with the therapeutic effect of single drug, the combination of chlorogenic acid and hormone drugs realizes the synergistic effect, and the therapeutic effect is better. Moreover, the combination can reverse the drug resistance of hormone drugs, and have good clinical application prospects.

The invention claimed is:

1. A combined medicine for treating cancer, comprising chlorogenic acid and a hormone drug in a unit preparation comprising the same or different dosage forms, and a pharmaceutically acceptable carrier, wherein said hormone drug is selected from fulvestrant, abarelix, degarelix, and combinations thereof, chlorogenic acid is administrated at 10-40 mg/kg, fulvestrant is administrated at 40 mg/kg, abarelix is administrated at 15 mg/kg, and degarelix is administrated at 30 mg/kg, and said cancer is hormone-dependent breast, prostate, ovarian, and/or cervical cancer(s).

2. The combined medicine according to claim 1, wherein a weight ratio of said chlorogenic acid and the hormone drug is 2:3-1:3, and the hormone drug is fulvestrant or degarelix.

3. The combined medicine according to claim 1, wherein said unit preparation is an injectable or oral formulation of drug.

* * * * *